US008182553B2

(12) United States Patent
Frykerås et al.

(10) Patent No.: US 8,182,553 B2
(45) Date of Patent: May 22, 2012

(54) PROCESS FOR PURIFICATION OF FATTY ACID ALKYL ESTERS AND USE OF AGENTS TO FACILITATE SUCH PURIFICATION

(75) Inventors: David Frykerås, Norrköping (SE); Jan Warnqvist, Kil (SE)

(73) Assignee: Alfa Laval Corporate AB, Lund (SE)

( * ) Notice: Subject to any disclaimer, the term of this patent is extended or adjusted under 35 U.S.C. 154(b) by 792 days.

(21) Appl. No.: 12/160,756

(22) PCT Filed: Jan. 11, 2007

(86) PCT No.: PCT/SE2007/000016
§ 371 (c)(1),
(2), (4) Date: Nov. 24, 2008

(87) PCT Pub. No.: WO2007/081269
PCT Pub. Date: Jul. 19, 2007

(65) Prior Publication Data
US 2009/0183421 A1    Jul. 23, 2009

(51) Int. Cl.
C10L 1/18    (2006.01)
C07C 67/58    (2006.01)
(52) U.S. Cl. .......................................... 44/308; 44/385
(58) Field of Classification Search .................... 44/308, 44/385
See application file for complete search history.

(56) References Cited

U.S. PATENT DOCUMENTS

| 5,972,057 A | 10/1999 | Hayafuji et al. |
| 6,242,620 B1 | 6/2001 | Elsasser et al. |
| 2005/0081436 A1* | 4/2005 | Bertram et al. ................ 44/605 |
| 2005/0204612 A1 | 9/2005 | Connemann et al. |
| 2006/0096159 A1 | 5/2006 | Bonsch et al. |

FOREIGN PATENT DOCUMENTS

| DE | 201 11 992 | 1/2003 |
| EP | 1 331 260 | 7/2003 |
| GB | 990 034 | 4/1965 |
| GB | 1306446 | 2/1973 |
| JP | 2004-307608 | 11/2004 |
| WO | WO 99/44977 | 9/1999 |
| WO | WO 2004/029016 | 4/2004 |
| WO | WO 2004/053036 | 6/2004 |
| WO | WO 2004/059315 | 7/2004 |
| WO | WO 2005/037969 | 4/2005 |
| WO | WO 2005/063954 | 7/2005 |

OTHER PUBLICATIONS

Ozkan, A. "Coagulation and flocculation characteristics of talc by different flocculants in the presence of cations," *Minerals Engineering* 16: 59-61 (2003).
Supplementary European Search Report for European Application No. EP 07 70 1102, dated Jan. 26, 2011.
Derwent English Abstract of DE 201 11 992, Week No. 200312.
Derwent English Abstract of WO 2004/029016, Week No. 200429.
Derwent English Abstract of WO 2004/053036, Week No. 200445.
"Flocculating Agents," *Kirk-Othmer Encyclopedia of Chemical Technology*, 11: 625-627 (1966).
Machine English Translation for JP 2004-307608 (Nov. 4, 2004).
"Mike Pelly's biodiesel method," http://journeytoforever.org/biodiesel_mike.hmtl (Nov. 18, 2005).
Patent Abstracts of Japan for JP 2004-307608 (Nov. 4, 2004).
Van Gerpen, J. et al. "Biodiesel Production Technology," *National Renewable Energy Laboratory* (http://www.osti.gov/bridge) *NREL/SR*-510-36244; Jul. 2004.
Wikipedia: Flocculation (http://en.wikipedia.org/wiki/flocculation) (Aug. 10, 2006).
Wikipedia: Emulsion (http://en.wikipedia.org/wiki/emulsifier) (Aug. 18, 2006).
Wikipedia: Deflocculant (http://en.wikipedia.org/wiki/deflocculant) (Aug. 18, 2006).
International Search Report mailed Apr. 24, 2007, for International Application No. PCT/SE2007/000016 (WO 2007/081269).
Swedish Search Report mailed Jul. 5, 2006, for Swedish Application No. 0600050-9.
INEOS Silicas brochure, Sorbsil ® R Silicas, Products for the Edible Oil Industry from web.archive.org's archives dated Oct. 17, 2006 available at http://web.archive.org/web/20061017063042/http://www.ineossilicas.com/downloads/Edible%20oil%20Brochure.pdf last visited on Sep. 22, 2011.
English-language Translation of Russian Office Action for Application No. 2008133039 dated Apr. 27, 2011.
English-language Translation of Russian Office Action for Application No. 2008133039 dated Dec. 1, 2010.
Wikipedia:Biodiesel (http://en.wikipedia.org/wiki/biodiesel) version dated Sep. 14, 2011.
English Translation of Russian Office Action for Application No. 2008133039 dated Apr. 27, 2011.

\* cited by examiner

*Primary Examiner* — Walter D Griffin
*Assistant Examiner* — Vishal Vasisth
(74) *Attorney, Agent, or Firm* — Finnegan, Henderson, Farabow, Garrett & Dunner LLP

(57) ABSTRACT

A method of purifying an organic solution comprising contacting a flocculating and sequestering agent with the organic solution, which organic solution comprises fatty acid alkyl esters. Also provided is a process for purification of the organic solution. The process comprises adding a flocculating and sequestering agent to the organic solution to facilitate the purification, and removing a portion from the organic solution, which portion comprises the flocculating and sequestering agent and impurities.

18 Claims, No Drawings

PROCESS FOR PURIFICATION OF FATTY ACID ALKYL ESTERS AND USE OF AGENTS TO FACILITATE SUCH PURIFICATION

This application is a national stage filing under 35 U.S.C. §371 of International Application No. PCT/SE2007/000016, filed on Jan. 11, 2007, which claims the benefit of priority of Swedish Application No. 0600050-9 filed on Jan. 12, 2006.

TECHNICAL FIELD OF THE INVENTION

The present invention relates to the use of certain agents to facilitate the purification of an organic solution of fatty acid alkyl esters. The present invention also relates to a process for purification of the fatty acid alkyl esters suitable for use as biodiesel.

TECHNICAL BACKGROUND

Fatty acid alkyl esters (mono alkyl esters of fatty acids such as methyl and ethyl esters of fatty acids) derived from vegetable oils or animal fats are known to be used as biodiesel. Known processes to produce such fatty acid alkyl esters comprise transesterification of triglycerides included in vegetable oils or animal fats in presence of an alcohol and a catalyst. It is well known in the art to use catalysts such as acid catalysts or more commonly alkali metal catalysts, e g sodium and potassium hydroxide or a metal alkoxide such as sodium or potassium methoxide. In fact, a metal alkoxide is a compound formed by the reaction of an alcohol with an alkali metal. In summary, the transesterification reaction can generally be described as follow:

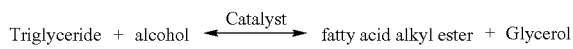

Triglyceride + alcohol $\xrightleftharpoons{\text{Catalyst}}$ fatty acid alkyl ester + Glycerol Among vegetable oils or animal fats that can be used are coconut oil, palm oil, seed oil, olive oil, sunflower oil, Soya oil, rapeseed oil and tallow. Suitable alcohols that can be used are aryl alcohols such as methanol, ethanol, propanol and butanol. Due to low cost, polarity and short chain, methanol is normally used in biodiesel production. Due to high activity, an alkali catalyst such as potassium hydroxide is usually used on industrial scale.

A well-known process for producing fatty acid alkyl esters comprises heating, for example, a vegetable oil to a temperature of normally between 30° C. and 110° C. The process further comprises adding an alcohol and a catalyst to the heated oil. The reaction will result in two phases, one including produced glycerol and the other including produced fatty acid alkyl ester. In addition, the process comprises removing the produced glycerol phase from the produced fatty acid alkyl ester phase.

Fatty acid alkyl esters produced according to known processes as described above normally comprises to high levels of impurities to comply with regulatory norms concerning fatty acid alkyl esters, e g the European norm EN-14214 for fatty acids methyl esters, which especially limits the impurities originating from the metals K, Na, Mg and Ca. Accordingly, there is a need for purification of the produced fatty acid alkyl esters. Known processes for purification include steps of neutralization and washing with water, which will wash out the impurities and produce fatty acid alkyl ester that complies with the regulatory norms and thus can be used as biodiesel. After each step of washing, the water can be separated from the fatty acid alkyl esters by any method known in the art such as await for the mixture to settle into two phases and thereafter drain off the water phase, or by centrifugation of the mixture. The total amount of water used can typically range from 20 to 100% water of the produced volume of fatty acid alkyl esters. After purification is completed, the traces of water comprised in the fatty acid alkyl esters have to be removed, for example, by re-heating the fatty acid alkyl esters. In addition, the water normally contains impurities that in turn needs to be removed, e g by filtrating the water and/or running the water through an ion exchange medium. The water can then be re-used or simply treated as wastewater.

A drawback with known procedures for purification of fatty acid alkyl esters by using water is that it is difficult to reduce the amount of metal impurities, e g calcium and magnesium impurities, to levels that comply with the regulatory norms concerning fatty acid alkyl esters, even when large amount of water is used for purification. Another drawback with known procedures of purifying the fatty acid alkyl esters using water is that the manufacturing of biodiesel, for example, requires high energy input and becomes time-consuming and costly, since the process, for example, requires a large amount of water for purification, which in turn needs to be purified.

SUMMARY OF THE INVENTION

In view of the aforementioned respects of known processes, an object of the present invention to provide a use of certain agents as well as a process for purification of fatty acid alkyl esters, which wholly or partly eliminate drawbacks of known techniques and which allow a production of fatty acid alkyl esters which is easy to handle resulting in high quality fatty acid alkyl esters suitable for use as biodiesel.

The invention is defined by the independent claims. Embodiments are evident from the dependent claims and from the following description and examples According to a first aspect, there is provided a use of a flocculating and sequestering agent as an agent facilitating the purification of an organic solution comprising fatty acid alkyl esters.

By a "flocculating and sequestering agent" is meant a reagent, usually a polyelectrolyte, added to a suspension to unite fine particles to form flocks. Further, the term includes an agent that can form several bonds to a metal ion, such as calcium and magnesium. In addition, the term also relates to an agent that forms an aqueous phase within an organic solution, which phase also attracts ions.

By an "organic solution of fatty acid alkyl esters" is understood a phase mainly comprising said fatty acid alkyl esters, but also small amounts of impurities such as the reactants and products of the transesterification process of triglycerides, eg soap, and ions and salts of metals.

The use of a flocculating and sequestering agent facilitates the removal of impurities such as calcium, magnesium, potassium and sodium impurities. In addition, the treatment with this flocculating and sequestering agent will not affect the acid number of the product, e g measured as free fatty acids and as other acidity, when added and removed properly. The acid number of free fatty acid methyl esters, for example, according to EN 14214 is restricted to 0.5 mg KOH/kg oil (for further discussion see below).

In one embodiment, the flocculating and sequestering agent is selected from the group consisting of polyaluminium coagulants.

Such polyaluminium coagulants facilitate to high extent a process, in which impurities, such as calcium, magnesium, potassium and sodium impurities, are to be removed, even from the nonpolar environment of the organic solution of fatty acid alkyl esters.

In one embodiment, the flocculating and sequestering agent is polyaluminium hydroxychloride.

Polyaluminium hydroxychloride facilitate to high extent the removal of impurities in the nonpolar environment of the organic solution of fatty acid alkyl esters, attracting metal ions such as calcium and magnesium ions. In addition, the polyaluminium hydroxychloride also forms an aqueous phase within the organic solution, which phase also attracts ions such as sodium and potassium ions. Moreover, the chloride ions aid in the removal of ions such as potassium and sodium.

In one embodiment, the organic solution is essentially anhydrous.

The term "essentially anhydrous" should be understood in the context of that no effective amount of free water is present in the organic solution. An effective amount is the amount that is sufficient to achieve a noticeable reduction in impurities according to the known purification processes using water to wash out impurities without addition of the flocculating and sequestering agent. Amounts of water known to be effective in such processes exceed 10% (by weight), typically around 10 to 60% (by weight) relative the organic solution. In its strict definition, the term means that no free water is needed for the purification and therefore not added to the organic solution during a purification process using the flocculating and sequestering agent. This means that the only water present at any time during the purification process is the water remaining from previous treatment such as a transesterification process, and additions of compounds during the purification. The addition of a flocculating and sequestering agent adds to the water content, and which addition depends on the added amount of agent. To some extent, small amounts of water, e g less than 1000 ppm by weight, will aid the creation of a phase within the organic solution, which phase attracts ions such as sodium and potassium ions. But, using to high amounts of water together with the flocculating and sequestering agent might affect the purification of the organic solution in a negative way, ie the flocculating and sequestering agent will not facilitate the removal of impurities.

Notwithstanding, in a preferred embodiment the maximum water content of the organic solution can be up to 10% (w/w). In a more preferred embodiment the maximum water content of the organic solution can be up to 9.5, 9.0, 8.5, 8.0, 7.5, 7.0, 6.5, 6.0, 5.5, 5.0, 4.5, 4.0, 3.5, 3.0, 2.5, 2.0, 1.5, 1.0, 0.5, 0.43 or 0.10% (w/w). In a more preferred embodiment, the water content is around 100 to 1000 ppm (w/w), and even more preferred around 500 ppm. Each of these embodiments will allow small amounts water as long as the total water content is well below an effective amount of water as mentioned above, and that the purification is not affected in a negative way.

According to a second aspect, there is provided a process for purification of an organic solution of fatty acid alkyl esters suitable for use as biodiesel, comprising:
  adding a flocculating and sequestering agent to the organic solution so as to facilitate the purification, and
  removing a portion from the organic solution, which portion comprises the flocculating and sequestering agent, and impurities.

Such a process for purification of fatty acid alkyl esters makes it possible to reduce the amount of metal impurities, e g calcium and magnesium impurities, to levels that comply with the regulatory norms concerning fatty acid alkyl esters.

In one embodiment of the process, the removing of the portion from the organic solution comprises a step of centrifugation of the organic solution so as to remove the flocculating and sequestering agent together with impurities, which are solid, polar and/or have different densities than the fatty acid alkyl esters.

Such a process will enable less energy input and becomes less time-consuming and less costly, as compared to the known processes using water to purify the organic solution. In addition, the efficiency of the process is easy to control and the process will demand very little monitoring. Moreover, the process can accomplish a system with low water content throughout the process. Such a process requires no water for purification, which in turn needs to be purified. In addition, the process yields a high amount of purified fatty acid alkyl esters that are suitable for use as biodiesel. Such a process will also enable the production of fatty acid alkyl esters without the need of separate neutralization with, for example, an acetic solution. Within the European norm (see above) there is a demand for the limitation of the acid number, which includes both free fatty and mineral acids in the biodiesel. The maximum value is 0.5 expressed as mg KOH/g of biodiesel. There is no demand for pH value in biodiesel, but the need for neutralization is assumed to create metal salts as a by-product of the neutralization. As an example, when fatty acid methyl esters are produced using methanol and alkali, the organic solution can contain rather high levels of alkali, which in turn leads to a pH up to around 11. In known processes, an acetic solution has to be added to the material.

In one embodiment of the process, the centrifugation is performed under low pressure in order to remove water from the organic solution.

In one embodiment of the process, essentially no water is added to the organic solution during the process to remove impurities.

The term "essentially no added water" should be understood in the context of the term "essentially anhydrous" as discussed above, ie the process comprises that the purification is performed in the absence of an effective amount of free water.

According to one embodiment, the water content of the organic solution of fatty acid alkyl esters throughout the process can be up to 10% (w/w). In a more preferred embodiment the maximum water content of the organic solution throughout the process can be up to 9.5, 9.0, 8.5, 8.0, 7.5, 7.0, 6.5, 6.0, 5.5, 5.0, 4.5, 4.0, 3.5, 3.0, 2.5, 2.0, 1.5, 1.0, 0.5 0.43 or 0.10% (w/w). In a more preferred embodiment, the water content is around 100 to 1000 ppm (w/w), and even more preferred around 500 ppm. Each of these embodiments will allow small amounts water as long as the total water content is well below an effective amount of water as mentioned above, and that the purification is not affected in a negative way.

In one embodiment of the process, the impurities comprise glycerol, soap, free fatty acid and/or metal impurities.

The process for purification of fatty acid alkyl esters makes it possible to reduce the amount of such impurities.

In one embodiment of the process, the metal impurities originate from metals comprising calcium, magnesium, potassium and/or sodium.

The process for purification of fatty acid alkyl esters makes it especially possible to reduce the amount of such metal impurities, and even to reduce the amounts of the metal impurities in the final product to be used as biodiesel, so as to comply with regulatory norms.

In one embodiment of the process, the flocculating and sequestering agent is selected from the group consisting of polyaluminium coagulants.

In one embodiment, the flocculating and sequestering agent is polyaluminium hydroxychloride.

The processes and the use according to the different aspects of the invention will now be described in more detail with reference to embodiments and examples.

DETAILED DESCRIPTION OF THE INVENTION AND EMBODIMENTS

The invention relates to the use of a flocculating and sequestering agent as an agent facilitating the purification of an organic solution comprising fatty acid alkyl esters, in particular mono alkyl esters of long fatty acids that are suitable for use as biodiesel. In one aspect, the invention also relates to a process for purification of the organic solution of fatty acid alkyl esters. The process makes use of a flocculating and sequestering agent to facilitate the purification, and removing a portion from the organic solution, which portion comprises the flocculating and sequestering agent, and impurities.

The organic solution of fatty acid alkyl esters to be purified is a product of vegetable oils or animal fats. In one embodiment, the oils or fats used are freshly refined oils or fats, meaning that the oils or fats have never been used. In another embodiment, the oils and fats used are re-used crude oils and fats such as oils that have been used as frying oils. Examples of vegetable oils freshly refined or re-used, are coconut oil, palm oil, olive oil, sunflower oil Soya oil and rapeseed oil.

The organic solution for purification can be produced according processes known in the art. Examples of such processes are those that comprise either acid or base catalysts. Examples of such catalysts are the hydroxides from sodium and potassium, alkoxides of potassium and sodium as well as anhydrous sulphuric and acetic acids. In a process of fatty acid alkyl esters, such as methyl esters of fatty acids, it is desirable to accomplish a system with low water content throughout the process. Such a system will disable production of process water, increase the produced yield of fatty acid alkyl esters, and decrease the production of by-products such as soaps. The final product to be used as biodiesel should preferably contain less than 500 ppm water. Accordingly, it is desirable to use catalysts not producing, or producing very small amount of water during preparation or theirs addition. One example of a catalyst in this context is the methoxide of sodium or potassium, which in turn can be formed by the reaction of methanol with sodium or potassium. One example of a process for producing methyl esters of fatty acid comprises heating a vegetable oil to a temperature of normally between 30° C. and 110° C., depending on the oil used, for example 80 to 90° C. when using used cooking oil, 50° C. when using rape seed oil and slightly lower when using more unsaturated oils. The process further comprises adding methanol and potassium or sodium methoxide to the heated oil. The amounts of potassium or sodium methoxide and methanol added depend on, for example, the amount of free fatty acid present in the oil, and the average molecular weight of the oil, each of which can be decided as is known to those skilled in the art. The methanol is usually added in excess. The reaction will result in two phases, one including produced glycerol and the other including produced methyl esters of fatty acids. In addition, the process comprises removing the produced glycerol phase, typically constituting around 15 to 20% (w/w) of the two phases, from the produced methyl ester phase, e g by gravity or two-phase centrifugation. Further, the methanol is removed by evaporation with help of under pressure or with a temperature above the boiling point of methanol. This process will yield an organic solution comprising up to 99% (w/w) methyl esters of fatty acids, which organic solution needs to be purified according to the invention.

Turning now to one aspect of the invention, wherein the flocculating and sequestering agent is used to aid the separation of impurities from the organic solution of fatty acid alkyl esters. The use of a flocculating and sequestering agent was surprisingly found to be useful in the almost nonpolar environments of the organic solution for attracting metal ions of various kinds. In addition, the flocculating and sequestering agent, was found to aid the separation of impurities other than metal ions from the organic solution, such as free fatty acids, soap and glycerol, which are polar as compared to the organic solution. Examples of such flocculating and sequestering agents are polyaluminium coagulants. Polyaluminium coagulants have a polymeric structure, and are known to be soluble in water. The length of the polymerised chain, molecular weight and number of ionic charges is determined by the degree of polymerisation. On hydrolysis, various mono- and polymeric species are formed. These highly polymerised sequestering agents include, for example: polyaluminium chloride, aluminium hydroxychloride, and polyaluminium hydroxychloride; marketed as, for example, Ekoflock 54, and Sweflock 10. The advantages of using polyaluminium coagulants are, for example, that they are cheap, non-carcinogenic and that they also will attract the ions from sodium and potassium in a chloride solution. Examples of other conceivable types of sequestering agents available on the market are polyaluminium ferric chloride, EDTA and acryl amides.

The flocculating and sequestering agent together with the impurities can be separated and removed from the organic solution by methods such as centrifugation and filtration or just by gravity letting the mixture settle into two phases, or by any other mechanical means as is known to those skilled in the art. In a preferred embodiment, the impurities are separated and removed by at least one step of centrifugation.

In one embodiment, polyaluminium hydroxychloride is used as the flocculating and sequestering agent, which is known as a satisfactory sequestering agent in water for metal ions, such as calcium and magnesium. The sequestering agent polyaluminium hydroxychloride was found to be useful in the nonpolar environment of the organic solution of fatty acid alkyl esters, attracting metal ions such as calcium and magnesium ions. In addition, the polyaluminium hydroxychloride also forms an aqueous phase within the organic solution, which phase also attracts ions such as sodium and potassium ions. Accordingly, even if less than 100% of the ions such as calcium and magnesium ions are sequestered by the flocculating and sequestering agent, a sufficient level of the remaining ions will be able to enter the aqueous phase. It should be noted that the traces of "water content" increases in the organic solution after addition of polyaluminium hydroxychloride that by its addition releases up to 1000 ppm (w/w) of water to the organic solution, depending on the amount of polyaluminium hydroxychloride added.

In one embodiment, the flocculating and sequestering agent is added when the pH in the organic solution is 9 to 12. Preferably, the pH is 10-11. Accordingly, the flocculating and sequestering agent is preferably added short after the transesterification process is completed and the methanol and glycerol has been removed, since the pH is high, around 10.3 to 10.5, and which pH will decrease in time.

In a preferred embodiment, the organic solution is essentially anhydrous, when the flocculating and sequestering agent is added, meaning that no effective amount of free water is present in the organic solution. An effective amount is the amount that is sufficient to achieve a noticeable reduction in impurities according to the known purification processes using water to wash out impurities without addition of the flocculating and sequestering agent. Amounts of water known to be effective in such processes exceed 10% (by weight), typically around 10 to 60% (by weight) relative the organic solution. In its strict definition, the term means that no free water is needed for the purification and therefore not added to the organic solution during a purification process using the flocculating and sequestering agent. This means that the only water present at any time during such purification process is the water remaining from previous treatment such as a transesterification process, and additions of compounds during the purification. The addition of a flocculating and sequestering agent adds to the water content, and which addition depends on the added amount of agent. To some extent, small amounts of water, e g less than 1000 ppm by weight, will aid the creation of a phase within the organic solution, which phase attracts ions such as sodium and potassium ions. But, using to high amounts of water together with the flocculating and sequestering agent might affect the purification of the organic solution in a negative way, ie the flocculating and sequestering agent will not facilitate the removal of impurities as will be exemplified by the comparative examples 7 to 10.

Notwithstanding, in one embodiment the maximum water content of the organic solution can be up to 10% (w/w). In a more preferred embodiment the maximum water content of the organic solution can be up to 9.5, 9.0, 8.5, 8.0, 7.5, 7.0, 6.5, 6.0, 5.5, 5.0, 4.5, 4.0, 3.5, 3.0, 2.5, 2.0, 1.5, 1.0, 0.5, 0.43 or 0.10% (w/w). In a more preferred embodiment, the water content is around 100 to 1000 ppm (w/w), and even more preferred around 500 ppm. Each of these embodiments will allow small amounts water as long as the total water content is well below an effective amount of water as mentioned above, and that the purification is not affected in a negative way. The concentration of water of the final product to be used as biodiesel should comply with the regulatory norms, and be equal or less than 500 ppm (w/w).

According to one aspect of the invention, the process for purification of the organic solution of fatty acid alkyl esters is provided. The process comprises a step of adding a flocculating and sequestering agent to the organic solution so as to facilitate the purification. In addition, the process comprises a step of removing a portion from the organic solution, which portion comprises the flocculating and sequestering agent, and impurities.

In one embodiment of the process, the step of removing a portion from the organic solution comprises a step of centrifugation so as to reduce the amount of impurities and flocculating and sequestering agent in the organic solution. One example of a centrifuges is a centrifuge with a closed bowl, e g model FM600 of Mann-Hummel, which is driven by and working under continuous flow of medium to be separated. The inlet of the centrifuge can be connected to a mixing tank/vessel and a pump, and the outlet for the purified solution can in turn also be connected to said tank/vessel.

It is noted that any suitable centrifuge as is known to those skilled in the art can be used. During the centrifugation, compounds that are solids, polar or/and have different densities than the fatty acid alkyl esters are separated and removed from the organic solution, such as the flocculating and sequestering agent and impurities. The total amount of impurities can constitute around 1 to 5% (w/w) of the organic solution. Examples of such compounds are impurities such as salts and ions of metals, free fatty acids, glycerol and soap. In one embodiment, using a bowl centrifuge (e g model FM600 of Mann-Hummel), a portion comprising free fatty acids, glycerol and soap together with the flocculating and sequestering agent create a phase in the bowl, which phase is polar as compared to the organic solution of fatty acid alkyl esters and which is drained off after centrifugation. Metal ions are also localized in this portion and thereby removed simultaneously. In one working embodiment, the centrifugation is performed using the bowl centrifuge of model FM600 (Mann-Hummel) at around 4200 rpm for six hours under continuous recirculation flow. In one embodiment, the centrifugation is performed under low pressure, e g −0.9 bar. The low pressure was shown to provide, for example, a reduction of water content, wherein the final water content in the organic solution is less than 500 ppm. The amount of impurities can, for example, be lowered from around 5% to 1% (w/w) of the organic solution. Typically, the portion drained off from the centrifuge constitutes approximately 1.1% (w/w) as compared to the initial batch weight. Using a flocculating and sequestering agent such as polyaluminium hydroxychloride in combination with separation by centrifugation lower to high extent the amount of impurities in the organic solution. The amount of added flocculating and sequestering agent depends on the initial levels of impurities. Saturated levels can be added, and even in excess, as calculated from the initial amount of impurities, which calculation is evident for those skilled in the art. Typical amount is above 0.5% (w/w), in particular 0.5 to 2.5% (w/w), of the organic solution to be purified.

The purified organic solution should comply with regulatory norms, eg the European norm EN-14214. In this norm the following limitations are stated: 5 mg/kg for potassium plus sodium and 5 mg/kg for calcium and magnesium. Examples of values before purification and after purification using a process comprising both centrifugation and addition of polyaluminium hydroxychloride are, as shown in the experimental part, for calcium plus magnesium 11 to 14 and 0.3 to 2.2, respectively, and for potassium and sodium 440 to 100 and 3.9 to 4.1, respectively.

As discussed above, one embodiment of the process comprises that essentially no water is added during the process. As will be evident from the experimental part, water can even affect the purification in a negative way.

In one embodiment, the addition of the flocculating and sequestering agent to the organic occurs before any centrifugation is performed. The addition is followed by at least one centrifugation step to remove the impurities together with the flocculating and sequestering agent. This method demands no or very little supervision by the operator, wherein the purification can be performed with just one step of removing impurities.

In another embodiment, the organic solution is subjected to at least one centrifugation step before any addition of the flocculating and sequestering agent occurs and further steps of removing impurities. The advantage with this method is to enable a pre-removal impurities, in particular soap and glycerol in almost pure form, before adding the flocculating and sequestering agent, and thereafter steps of centrifugation.

According to an additional aspect of the invention, there is provided a process for producing an organic solution comprising fatty acid alkyl esters, in particular mono alkyl esters of long fatty acids that are suitable for use as biodiesel. The process comprises producing the organic solution to be purified as discussed above, and purifying this organic solution according to the aspects of the invention regarding purification.

EXAMPLES

The invention will now be illustrated further through the non-limiting recital of experiments conducted in accordance therewith. In these experiments the aspects of purification with or without adding a flocculating and sequestering agent were tested as well as different concentrations of the same.

Examples 1 to 6

Experimental Procedures

Each one of the experiment of examples 1 to 6 was based on a batch of organic solution of fatty acid methyl esters produced using one embodiment of above described process for transesterification, wherein sodium or potassium methoxide was used as the catalyst as well as methanol as the alcohol, The catalyst added was for potassium methylate 0.64% by weight of organic solution, and for sodium methylate 0.45% by weight. Methanol was added at a stoichiometric surplus of 50% by weight. After the transesterification was completed, the glycerol phase was drained off and the excess of methanol was removed under low pressure (−0.9 bar) to leave a remaining batch of the organic solution for purification. The batch size for each experiment was around 3000 kg.

Experimental Conditions for Purification

For all experiments, the centrifugation was performed using a bowl centrifuge (model FM600 of Mann-Hummel) at 4,200 rpm for six hours at 55° C. under low pressure (−0.9 bar).

Polyaluminium hydroxychloride (cat no 1327-41-9, Eka Nobel) was used as the flocculating sequestering and agent. The amount added was from 0 to 2.25% by weight organic solution.

Polyaluminium hydroxychloride was added following the transesterification process and after the glycerol and the excess of methanol has been removed, when pH still is high, which pH was determined to be around 10.3 to 10.5.

Metal Content Analysis

The metal levels for Mg, Ca, Na and K were determined with ICP analysis (inductive coupled plasma with argon) using an instrument from Spectro GmbH. The analyses were performed based on the standard methods described by: ASTM D 4951-96, ASTM 5708-95a, ASTM 5185-95, DIN 51390-4, DIN 51391-3 and DIN 51790-6, whereby the spectrum lines 183,801/393,366, 285,213, 589,592 and 766.490 nm were used to determine the metal content concentrations for Ca, Mg, Na and K, respectively, which determination of concentrations is evident for the person skilled in the art.

Water Content Analysis

The water content was analyzed volumetrically by using calcium hydride ($CaH_2$). The hydride reacts with the water forming a gas pressure, which was measured by a special gauge for this purpose (the gauge meter in the so called Mobil water test kit, no 429950 produced by Signum/ExxonMobil).

Results: Examples 1 to 5

From the data shown in table 1, it is evident that the metals calcium plus magnesium and potassium plus sodium can amount around 20 and 100-450 mg/kg, respectively, after production of the organic solution comprising fatty acid alkyl esters before any purification. After treating the material with polyaluminium hydroxychloride followed by centrifugation the metal levels were to high extent reduced.

In example 3, the results were obtained by a step of centrifugation, but without addition of any flocculating and sequestering agent. The results show that the metal levels are reduced to some extent, but not to the levels obtained by using the purification combination of centrifugation and addition of a flocculating and sequestering agent.

For example 5, it should be noted that the results were obtained by using a slightly malfunctioning centrifuge.

Results: Example 6

In one experiment the water content of the organic solution was analyzed. The water content was as highest right before centrifugation and was determined to be 0.43% (w/w). After centrifugation for two hour, the water content was 0.23% (w/w) and after the centrifugation was completed the water content was determined to be 0.12% (w/w). The reason for the relatively high amount of water after the completed centrifugation was shown to be a result of a malfunctioning centrifuge. In other experiments the final water content have been determined to be lower than 1000 ppm (w/w), and the final product to be less than 500 ppm (data not shown).

Comparative Examples 7 to 10

Experimental Procedures

Each one of the experiments of examples 7 to 10 was based on a batch of organic solution of fatty acid methyl esters produced as mentioned above in examples 1 to 6. For each experiment, rapeseed oil was used as the starting material. The amount of biodiesel used for purification in each experiment was 100 g per experiment. The purification of the produced organic solution was performed in a similar way as described in examples 1 to 6, with the exception that the step of removal of the portion comprising the impurities was not performed by centrifugation. Instead, the organic solution was washed with water. The washing comprised mixing water with the organic solution, and removing the water from the organic solution. Three steps of washing were performed, wherein 20% (w/w) of water was added and removed in each step. This process resembles methods in the art in which water is used to wash the organic solution. One difference compared to the known methods was that a flocculating and sequestering agent was mixed into the organic solution before any washing with water occurred. The step of mixing flocculating and sequestering agent was performed before the steps of washing. After the washing with water, the remaining traces of water were removed by leaving the organic solution in a water bath at 50° C. until the water content was below 500 ppm.

Results: Examples 7 to 10

TABLE 1

| Example number | Origin of organic solution of fatty acid methyl esters | Initial content of Ca + Mg/Na + K (mg/kg) | Polyaluminium hydroxychloride (% (w/w)) | Final content of Ca + Mg/Na + K (mg/kg) |
| --- | --- | --- | --- | --- |
| 1 | Rape seed oil | 14.3/122 | 0.5 | 7.5/8.7 |
| 2 | Used cooking oil | 1.9/441 | 2.25 | 0.3/5.0 |
| 3 | Used cooking oil | 2.2/441 | 0 | 2.2/29.1 |
| 4 | Refined cooking oil | 0.5/27 | 0.64 | 1.1/4.1 |
| 5 | Rape seed oil | 6/25 | 0.7 | 1.7/8.3 |

TABLE 2

| | Example no | | | |
| --- | --- | --- | --- | --- |
| | 7 | 8 | 9 | 10 |
| Amount of added Al(OH)Cl (% w/w) | 0 | 0.5 | 0.7 | 1.0 |
| Amount of residual | 9.9 | 14.2 | 7.6 | 13.2 |

TABLE 2-continued

| | Example no | | | |
|---|---|---|---|---|
| | 7 | 8 | 9 | 10 |
| Na + K (mg/kg) | | | | |
| Amount of residual Ca + Mg (mg/kg) | 4.2 | 3.5 | 4.2 | 3.8 |
| Amount of residual Cl (mg/kg) | <1 | <1 | <1 | <1 |

From the data shown in table 2, it is evident that washing water (3×20% w/w) without centrifugation together with the flocculating and sequestering agent will not work properly in reducing the metal impurities, even as compared to washing with water without any addition of flocculating and sequestering agent. Only the values for calcium plus magnesium are of approved levels. The reason for the relatively high remaining levels of metal impurities might be due to poor water solubility properties of the complexes formed by the flocculating and sequestering agent. Moreover, as seen from the low remaining chloride concentration of the final product, the mechanism of using washing water might not allow the potassium plus sodium to form chlorides together with the flocculating and sequestering agent. Instead, the chloride ions seem to preferably migrate into the water and thereby being washed away without the metals and the flocculating and sequestering agent. The concentration of chloride ions before purification and after the flocculating and sequestering agent has been added can be up 11 mg/kg.

These results also indicate that addition of water with the flocculating and sequestering agent might affect the purification of the organic solution in a negative way, ie the flocculating and sequestering agent will not facilitate the removal of impurities, even when purification process comprises a centrifugation step.

Examples 11 and 12

Experimental Procedures

Each one of the experiment of examples 11 and 12 was based on a batch of organic solution of fatty acid methyl esters produced, purified and analyzed as mentioned above in examples 1 to 6, with the exceptions of a slightly different amount of added catalyst and that batch size was around 3000 kg in example 11 and around 16000 kg in example 12. In example 11, the catalyst was potassium methylate in an amount of around 0.78% by weight of organic solution. In example 12, the catalyst was sodium methylate in an amount of around 0.51% by weight of organic solution.

Results: Examples 11 and 12

TABLE 3

| Example number | Origin of organic solution of fatty acid methyl esters | Poly-aluminium hydroxy-chloride (% (w/w)) | Final content of Na + K (mg/kg) | Final content of Ca + Mg (mg/kg) |
|---|---|---|---|---|
| 11 | Rape seed oil | 0.6 | 1.5 | <0.5 |
| 12 | Sunflower oil | 0.5 | 4.4 | 0.4 |

From the data shown in table 3, it is evident that by treating the organic solution of fatty acid methyl esters with polyaluminium hydroxychloride followed by centrifugation the metal levels were to high extent reduced, even in case of sunflower oil as the origin of organic solution.

The invention claimed is:

1. A method of purifying an organic solution, comprising contacting a flocculating and sequestering agent chosen from polyaluminum coagulants with the organic solution when the pH of the organic solution ranges from 9 to 12, wherein the organic solution comprises fatty acid alkyl esters, wherein the water content of the organic solution is equal or less than 5% by weight wherein the organic solution is suitable for biodiesel production.

2. The method of claim 1, wherein the flocculating and sequestering agent is polyaluminium hydroxychloride.

3. The method of claim 1, wherein the water content of the organic solution is equal or less than 4.5% (w/w).

4. A process for purification of an organic solution of fatty acid alkyl esters suitable for use as biodiesel, comprising:
adding a flocculating and sequestering agent chosen from polyaluminum coagulants to the organic solution when the pH of the organic solution ranges from 9 to 12, and
removing a portion from the organic solution, which portion comprises the flocculating and sequestering agent and impurities,
wherein the water content of the organic solution of fatty acid alkyl esters throughout the process is equal or less than 5% by weight.

5. The process of claim 4, wherein the removing of the portion from the organic solution comprises a step of centrifugation of the organic solution to remove the flocculating and sequestering agent together with impurities, which are solid, polar and/or have different densities than the fatty acid alkyl esters.

6. The process of claim 5, wherein the centrifugation is performed under low pressure to remove water from the organic solution.

7. The process of claim 4, wherein the water content of the organic solution of fatty acid alkyl esters throughout the process is equal or less than 4.5% (w/w).

8. The process of claim 4, wherein the impurities comprise glycerol, soap, free fatty acid and/or metal impurities.

9. The process of claim 8, wherein the metal impurities originates from metals comprising calcium, magnesium, potassium and/or sodium.

10. The process of claim 9, wherein the flocculating and sequestering agent is polyaluminium hydroxychloride.

11. The method of claim 3, wherein the water content of the organic solution ranges from about 100 to about 1000 ppm (w/w).

12. The method of claim 3, wherein the water content of the organic solution is about 500 ppm (w/w).

13. The process of claim 7, wherein the water content of the organic solution of fatty acid alkyl esters throughout the process ranges from about 100 to about 1000 ppm (w/w).

14. The process of claim 7, wherein the water content of the organic solution of fatty acid alkyl esters throughout the process is about 500 ppm (w/w).

15. The method of claim 1, wherein the water content of the organic solution is equal or less than 2.0% (w/w).

16. The method of claim 1, wherein the water content of the organic solution is equal or less than 0.5% (w/w).

17. The method of claim 4, wherein the water content of the organic solution is equal or less than 2.0% (w/w).

18. The method of claim 4, wherein the water content of the organic solution is equal or less than 0.5% (w/w).

* * * * *

UNITED STATES PATENT AND TRADEMARK OFFICE
CERTIFICATE OF CORRECTION

PATENT NO. : 8,182,553 B2  
APPLICATION NO. : 12/160756  
DATED : May 22, 2012  
INVENTOR(S) : David Frykerås et al.

Page 1 of 1

It is certified that error appears in the above-identified patent and that said Letters Patent is hereby corrected as shown below:

On the Title Page, column 1, after item (65) and before item (51), insert the following:

--(30)    Foreign Application Priority Data  
Jan. 12, 2006   (SE)   .............................   0600050-9--.

Signed and Sealed this  
Second Day of October, 2012

David J. Kappos  
*Director of the United States Patent and Trademark Office*